(12) United States Patent
De La Mettrie

(10) Patent No.: US 6,387,855 B1
(45) Date of Patent: May 14, 2002

(54) WASHING AND CONDITIONING COMPOSITIONS BASED ON SILICON AND HYDROPHOBIC GUAR GUM

(75) Inventor: Roland De La Mettrie, Le Vésinet (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/446,962

(22) Filed: Jan. 31, 2000

(30) Foreign Application Priority Data

Jul. 2, 1997 (FR) .............................. 97 08346

(51) Int. Cl.$^7$ .............................. A61K 7/075
(52) U.S. Cl. .............. 510/122; 510/122; 510/119; 510/130; 510/137; 510/138; 510/151
(58) Field of Search .................. 510/122, 151, 510/152, 119, 130, 137, 138

(56) References Cited

U.S. PATENT DOCUMENTS

| | | | |
|---|---|---|---|
| 2,528,378 A | 10/1950 | Mannheimer | 260/309.6 |
| 2,781,354 A | 2/1957 | Mannheimer | |
| 4,693,935 A | 9/1987 | Mazurek | 428/352 |
| 4,728,571 A | 3/1988 | Clemens et al. | 428/352 |
| 4,870,167 A | 9/1989 | Zody et al. | 536/114 |
| 4,960,876 A | 10/1990 | Molteni et al. | 536/114 |
| 4,972,037 A | 11/1990 | Garbe et al. | 526/245 |
| 5,179,083 A | 1/1993 | Zody et al. | 514/54 |
| 5,275,755 A * | 1/1994 | Sebag et al. | 252/174.15 |
| 5,500,152 A * | 3/1996 | Helliwell | 252/547 |

FOREIGN PATENT DOCUMENTS

| | | | |
|---|---|---|---|
| EP | 0 186 507 | 7/1986 | |
| EP | 0 281 360 A1 * | 7/1988 | 37/14 |
| EP | 0 337 354 | 10/1989 | |
| EP | 0 412 704 | 2/1991 | |
| EP | 0 412 707 | 2/1991 | |
| EP | 0 582 152 | 2/1994 | |
| FR | 2 270 846 | 12/1975 | |
| FR | 2 383 660 | 10/1978 | |
| FR | 2 470 596 | 6/1981 | |
| FR | 2 519 863 | 7/1983 | |
| FR | 2 598 611 | 11/1987 | |
| FR | 2 641 185 | 7/1990 | |
| FR | 2 137 684 | 12/1992 | |
| WO | WO 93/23009 | 11/1993 | |
| WO | WO 93/23446 | 11/1993 | |
| WO | WO 95/00578 | 1/1995 | |

OTHER PUBLICATIONS

Charles Todd et al., "Volatile Silicone Fluids for Cosmetic Formulations", Cosmetics and Toiletries, vol. 91, Jan. 1976, pp. 29–32.
English language Derwent Abstract of FR 2 137 684, 1998.
English language Derwent Abstract of FR 2 270 846, 1999.
English language Derwent Abstract of FR 2 383 660, 1999.
English language Derwent Abstract of FR 2 470 596, 1999.
English language Derwent Abstract of FR 2 519 863, 1999.
English language Derwent Abstract of FR 2 598 611, 1999.
English language Derwent Abstract of FR 2 641 185, 1999.

* cited by examiner

*Primary Examiner*—Yogendra N. Gupta
*Assistant Examiner*—Eiśa Elhilo
(74) *Attorney, Agent, or Firm*—Finnegan, Henderson, Farabow, Garrett & Dunner.L.L.P.

(57) ABSTRACT

The invention concerns compositions for washing and conditioning keratinous materials, particularly hair and/or skin, based on silicon, a surfactant and a hydrophobic guar gum, and the washing and conditioning methods using said compositions.

32 Claims, No Drawings

WASHING AND CONDITIONING COMPOSITIONS BASED ON SILICON AND HYDROPHOBIC GUAR GUM

This application was filed under 35 U.S.C. §371 based on International Application Number PCT/FR98/01315, filed Jun. 23, 1998, which claimed priority to French Patent Application FR 97/08,346, filed Jul. 2, 1997.

The present invention relates to washing and conditioning compositions for keratin substances, in particular the hair and/or the skin, based on silicone, on surfactant and on a hydrophobic galactomannan gum, as well as to washing and conditioning processes using these compositions.

Compositions for washing keratin substances, in particular shampoos, are well known in the state of the art. It has already been proposed in the past to use silicones (conditioners) in such compositions in order to give the treated substances, in particular the hair, good cosmetic properties such as softness, sheen and easy disentangling.

Given the insoluble nature of the silicones which can be used in washing and conditioning compositions, it is desirable to keep the silicones in uniform dispersion in the medium without, however, causing the viscosity to fall or reducing the compositions' detergent and foaming properties. The silicones must also be conveyed onto the keratin substances treated in order to give these substances, once the silicones have been applied, properties of softness, sheen and disentangling.

Few means exist at the present time for effectively maintaining insoluble silicones in suspension, since this is a difficult problem to solve; in this regard, it has already been proposed to use long-chain ester derivatives (pearlescent agents) or polysaccharides such as xanthan gum (gelling agents). However, pearlescent agents have crystallization problems which entail a change (increase) in the viscosity of the compositions over time; gelling agents also have drawbacks, namely, on the one hand, that the foam of detergent compositions containing xanthan gum is difficult to develop (poor initiation of foaming), and that, on the other hand, the compositions do not have a smooth texture and flow in blobs, which users do not find particularly agreeable.

The Applicant has discovered, and this forms the subject of the invention, that by using at least one hydrophobic galactomannan gum in washing compositions based on insoluble silicones and on surfactants, it was possible to obtain compositions with very good homogeneity and improved stability, as well as a viscosity which is satisfactory for application to keratin substances.

The compositions thus prepared also have good detergent and foaming properties and give keratin substances, in particular the hair and/or the skin, great softness.

When they are applied to the hair, in addition to their washing properties, these compositions have hair conditioning properties, i.e. treated hair is shiny, disentangles easily, feels soft, and has volume. The hair has a natural appearance and is not lank.

The compositions according to the invention are stable: in particular, no release of silicone or uncontrolled thickening of the composition over time takes place. Finally, the compositions have a soft, non-runny texture. The lather is airy and rinses out easily.

The subject of the invention is thus novel washing and conditioning compositions based on silicone, on surfactants and on hydrophobic galactomannan gum described below.

Another subject of the invention consists of the washing and conditioning process using such compositions.

The subject of the invention is also the use of a hydrophobic galactomannan gum as an agent for suspending a silicone in a washing and conditioning composition containing surfactants in a cosmetically acceptable aqueous medium.

Other subjects of the invention will become apparent on reading the description and the examples which follow.

The compositions for washing and conditioning keratin substances, in particular the hair and the skin, in accordance with the invention comprise, in a cosmetically acceptable aqueous medium, at least one silicone, at least one surfactant with detergent properties and at least one hydrophobic galactomannan gum.

Galactomannans are polysaccharides mainly composed of galactose and mannose units. The main source of galactomannans is the endosperms of certain seeds of legumes such as guar, carob, etc. The galactomannans are preferably chosen from guar gums.

The galactomannan gums which can be used according to the invention may be soluble or insoluble in the compositions, but are preferably insoluble.

The expression "degree of substitution" means the average number of substituted hydroxyl groups on each anhydroglycoside unit of the galactomannan.

The expression "molar substitution" means the average number of moles of substituents on each anhydroglycoside unit of the galactomannan.

According to the invention, the expression "hydrophobic galactomannan gums" defines galactomannan gums which contain hydrophobic substituents.

Preferably, these galactomannan gums according to the invention contain hydrophilic substituents and hydrophobic substituents.

The galactomannans according to the invention preferably have a total molar substitution of greater than 0.7 and comprise from 0.7 to 4 hydrophilic substituents and from 0.0001 to 0.02 hydrophobic substituents per anhydroglycoside unit. The molar ratio of the hydrophilic substituents/hydrophobic substituents is preferably between 35:1 and 40,000:1.

According to the invention, the hydrophilic substituents can be chosen from $C_1$–$C_4$ alkyl groups, hydroxymethyl, hydroxyethyl, hydroxypropyl, hydroxybutyl and carboxymethyl groups and amino and carboxylic groups.

According to the invention, the hydrophobic substituents can be chosen from linear or branched alkyls and alkenyls containing from 8 to 60 carbon atoms and preferably from 10 to 32 carbon atoms, and mixtures thereof, and the alkyl or alkenyl groups can be substituted with one or more hydroxyls.

The hydrophilic and hydrophobic substituents can either be linked directly via a carbon-carbon bond to the anhydroglycoside unit, or can be linked via an ether, urethane, ester, amide or acyl bond and preferably via an ether bond.

More particularly, the galactomannans according to the invention have a total molar substitution ranging from 0.9 to 2.01 and comprise from 0.9 to 2 hydrophilic substituents and from 0.0005 to 0.01 hydrophobic substituents per anhydroglycoside unit. The molar ratio of the hydrophilic substituents/hydrophobic substituents is between 90:1 and 4000:1.

More particularly, the hydrophilic substituent is the hydroxypropyl group and the hydrophobic substituent is a linear alkyl containing from 16 to 28 carbon atoms or a mixture of such alkyls, optionally linked to the anhydroglycoside units via an ether bond and comprising a hydroxyl group.

These compounds can be prepared according to the process described in U.S. Pat. Nos. 4,960,876 and 4,870,167.

Hydrophobic galactomannan gums which can be used in the context of the present invention are, in particular, guar gums sold under the name Esaflor HM 22 by the company Lamberti or under the name Jaguar XC 95-3 by the company Rhône-Poulenc.

The silicones which can be used in accordance with the invention are, in particular, polyorganosiloxanes that are insoluble in the composition and can be in the form of oils, waxes, resins or gums.

The organopolysiloxanes are defined in greater detail in Walter Noll's "Chemistry and Technology of Silicones" (1968) Academic Press. They can be volatile or non-volatile.

If volatile, the silicones are more particularly chosen from those having a boiling point of between 60° C. and 260° C., and even more particularly from:

(i) cyclic silicones containing from 3 to 7 and preferably from 4 to 5 silicon atoms. These are, for example, octamethylcyclotetrasiloxane sold in particular under the name "Volatile Silicone 7207" by Union Carbide or "Silbione 70045 V 2" by Rhône-Poulenc, decamethylcyclopentasiloxane sold under the name "Volatile Silicone 7158" by Union Carbide, and "Silbione 70045 V 5" by Rhône-Poulenc, and mixtures thereof.

Mention may also be made of cyclocopolymers of the dimethylsiloxanes/methylalkylsiloxane type, such as "Volatile Silicone FZ 3109" sold by the company Union Carbide, with the chemical structure:

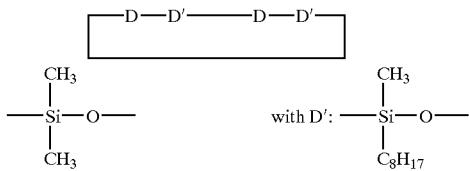

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; (ii) linear volatile silicones having 2 to 9 silicon atoms and having a viscosity of less than or equal to $5 \times 10^{-6}$ m$^2$/s at 25° C. An example is decamethyltetrasiloxane sold in particular under the name "SH 200" by the company Toray Silicone. Silicones belonging to this category are also described in the article published in Cosmetics and Toiletries, Vol. 91, Jan. 76, pp. 27–32, Todd & Byers "Volatile Silicone Fluids for Cosmetics".

Non-volatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5 \times 10^{-6}$ to 2.5 m$^2$/s at 25° C. and preferably $1 \times 10^{-5}$ to 1 m$^2$/s.

Among these polyalkylsiloxanes, mention may be made, in a non-limiting manner, of the following commercial products:

the Silbione oils of the series 47 and 70 047 or the Mirasil oils sold by Rhône-Poulenc, such as, for example, the oil 70 047 V 500 000;

the oils of the Mirasil series sold by the company Rhône-Poulenc;

the oils of the 200 series from the company Dow Corning such as, more particularly, DC200 with a viscosity of 60,000 Cst;

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

In this category of polyalkylsiloxanes, mention may also be made of the products sold under the names "Abil Wax 9800 and 9801" by the company Goldschmidt, which are poly($C_1$–$C_{20}$)alkylsiloxanes.

The polyalkylarylsiloxanes are chosen particularly from linear and/or branched polydimethylmethylphenylsiloxanes and polydimethyldiphenylsiloxanes with a viscosity of from $1 \times 10^{-5}$ to $5 \times 10^{-2}$ m$^2$/s at 25° C.

Among these polyalkylarylsiloxanes, mention may be made, by way of example, of the products sold under the following names:

the Silbione oils of the 70 641 series from Rhône-Poulenc;

the oils of the Rhodorsil 70 633 and 763 series from Rhône-Poulenc;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicone gums which can be used in accordance with the invention are, in particular, polydiorganosiloxanes having high number-average molecular masses of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:

polydimethylsiloxane polydimethylsiloxanes/methylvinylsiloxane gums, polydimethylsiloxane/diphenylmethylsiloxane, polydimethylsiloxane/phenylmethylsiloxane, polydimethylsiloxane/diphenylsiloxane/methylvinylsiloxane.

Products which can be used more particularly in accordance with the invention are mixtures such as:

mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in SF 1202 Silicone Fluid oil corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of a gum SE 30 defined above, having a viscosity of 20 m²/s, and an oil SF 96, with a viscosity of 5×10⁻⁶ m²/s. This product preferably contains 15% SE 30 gum and 85% SF 96 oil.

The organopolysiloxane resins which can be used in accordance with the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon-based group having from 1 to 16 carbon atoms or a phenyl group. Among these products, those particularly preferred are the ones in which R denotes a $C_1$–$C_4$ lower alkyl radical, more particularly methyl, or a phenyl radical.

Among these resins, mention may be made of the product sold under the name "Dow Corning 593" or those sold under the names "Silicone Fluid SS 4230 and SS 4267" by the company General Electric, which are silicones of dimethyl/trimethyl siloxane structure.

Mention may also be made of the trimethyl siloxysilicate resins sold in particular under the names X22-4914, X21-5034 and X21-5037 by the company Shin-Etsu.

The organomodified silicones which can be used in accordance with the invention are silicones as defined above and containing in their structure one or more organofunctional groups attached via a hydrocarbon-based radical.

Among the organomodified silicones, mention may be made of polyorganosiloxanes containing:

polyethylenoxy and/or polypropylenoxy groups optionally containing $C_6$–$C_{24}$ alkyl groups, such as the products known as dimethicone copolyol sold by the company Dow Corning under the name DC 1248 or the oils Silwet L 722, L 7500, L 77 and L 711 from the company Union Carbide and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$–$C_4$ aminoalkyl groups;

thiol groups such as the products sold under the names "GP 72 A" and "GP 71" from Genesee;

alkoxylated groups such as the product sold under the name "Silicone Copolymer F-755" by SWS Silicones and Abil Wax 2428, 2434 and 2440 by the company Goldschmidt;

hydroxyl groups such as the polyorganosiloxanes containing a hydroxyalkyl function, described in French patent application FR-A-85/16334 corresponding to formula (V):

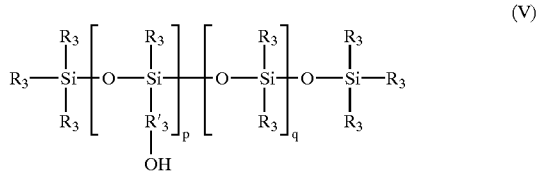

(V)

in which the radicals $R_3$, which may be identical or different, are chosen from methyl and phenyl radicals; at least 60 mol % of the radicals $R_3$ denoting methyl; the radical $R'_3$ is a divalent $C_2$–$C_{18}$ hydrocarbon-based alkylene chain unit; p is between 1 and 30 inclusive; q is between 1 and 150 inclusive;

acyloxyalkyl groups such as, for example, the polyorganosiloxanes described in French patent application FR-A-2 641 185 and corresponding to formula (VI):

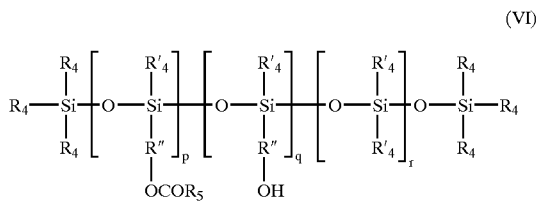

(VI)

in which:
$R_4$ denotes a methyl, phenyl, —OCOR$_5$ or hydroxyl group, only one of which radicals $R_4$ per silicon atom may be OH;
$R'_4$ denotes methyl, phenyl; at least 60 mol % of all of the radicals $R_4$ and $R'_4$ denoting methyl;
$R_5$ denotes $C_8$–$C_{20}$ alkyl or alkenyl;
R" denotes a linear or branched, divalent $C_2$–$C_{18}$ hydrocarbon-based alkylene radical;
r is between 1 and 120 inclusive;
p is between 1 and 30;
q is equal to 0 or is less than 0.5 p, p+q being between 1 and 30; the polyorganosiloxanes of formula (VI) can contain groups:

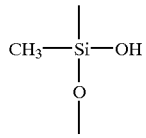

in proportions not exceeding 15% of the sum p+q+r.

The compounds of formula (VI) can be prepared by esterification of polyorganosiloxanes containing a hydroxyalkyl function of formula (V) above.

anionic groups of carboxylic type, such as, for example, in the products described in patent EP 186 507 from the company Chisso Corporation, or of alkylcarboxylic type, such as those present in the product X-22-3701E from the company Shin-Etsu; 2-hydroxyalkyl sulphonate; 2-hydroxyalkyl thiosulphate such as the products sold by the company Goldschmidt under the names "Abil S201" and "Abil S255".

hydroxyacylamino groups, such as the polyorganosiloxanes described in application EP 342 834. Mention may be made, for example, of the product Q2-8413 from the company Dow Corning.

According to the invention, silicones can also be used comprising a polysiloxane portion and a portion consisting of a non-silicone organic chain, one of the two portions constituting the main chain of the polymer, the other being grafted onto the said main chain. These polymers are described, for example, in patent applications EP-A-412,704, EP-A-412,707, EP-A-640,105, WO 95/00578, EP-A-582,152 and WO 93/23009 and U.S. Pat. Nos. 4,693,935, 4,728,571 and 4,972,037. These polymers are preferably anionic or nonionic.

Such polymers are, for example, copolymers which can be obtained by radical polymerization starting with a monomer mixture consisting of:

a) 50 to 90% by weight of tert-butyl acrylate;

b) 0 to 40% by weight of acrylic acid;
c) 5 to 40% by weight of silicone macromer of formula:

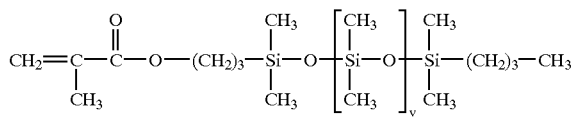

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

According to the invention, all of the silicones can also be used in the form of emulsions.

The polyorganosiloxanes which are particularly preferred in accordance with the invention are:
  nonvolatile silicones chosen from the family of polyalkyl-siloxanes containing trimethylsilyl end groups, such as oils having a viscosity of between 0.2 and 2.5 m²/s at 25° C., such as the oils of the series DC200 from Dow Corning, in particular that with a viscosity of 60,000 Cst, of the series Silbione 70047 and 47 and more particularly the oil 70 047 V 500,000, which are sold by the company Rhône-Poulenc, polyalkylsiloxanes containing dimethylsilanol end groups, such as dimethiconol, or polyalkylarylsiloxanes such as the oil Silbione 70641 V 200 sold by the company Rhône-Poulenc;
  mixtures of organopolysiloxanes and of cyclic silicones, such as the product Q2 1401 sold by the company Dow Corning, and the product SF 1214 sold by the company General Electric;
  mixtures of two PDMSs of different viscosities, in particular of a gum and an oil, such as the product SF 1236 sold by the company General Electric;
  the polyorganosiloxane resin sold under the name Dow Corning 593;
  polysiloxanes containing amine groups, such as amodimethicones or trimethylsilylamodimethicones.

The surfactants which can be used in the washing and conditioning compositions in accordance with the invention can be chosen from anionic, amphoteric, zwitterionic and nonionic surfactants or mixtures thereof with detergent properties.

In the context of the present invention, their nature is not a really critical feature.

The surfactants which are suitable for carrying out the present invention are, in particular, the following:
(i) Anionic Surfactant(s)
Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of alkylpolyglycosides containing a sulphate, sulphonate, succinate or sulphosuccinate group, alkyl-D-galactosiduronic acids and their salts, and polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and salts thereof, in particular those comprising from 2 to 50 ethylene oxide groups, and mixtures thereof.

Among the anionic surfactants, it is preferred according to the invention to use alkyl sulphate and alkyl ether sulphate salts and mixtures thereof.
(ii) Nonionic Surfactant(s)
Nonionic surfactants are likewise compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, optionally oxyalkylenated ($C_8$–$C_{20}$)alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.
(iii) Amphoteric Surfactant(s)
The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example carboxylate, sulphonate, sulphate, phosphate or phosphonate); mention may also be made of ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido($C_1$–$C_6$) alkylsulphobetaines.

Among the amine derivatives, mention may be made of the products sold under the name Miranol, as described in U.S. Pat. Nos. 2,528,378 and 2,781,354 and having the structures:

$$R_2\text{—CONHCH}_2\text{CH}_2\text{—N}(R_3)(R_4)(\text{CH}_2\text{COO—}) \quad (2)$$

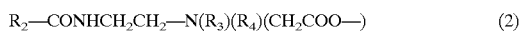

in which: $R_2$ denotes an alkyl radical derived from an acid $R_2$—COOH present in hydrolysed coconut oil, a heptyl, nonyl or undecyl radical, $R_3$ denotes a β-hydroxyethyl group and $R_4$ denotes a carboxymethyl group; and $$R_{2'}\text{—CONHCH}_2\text{CH}_2\text{—N(B)(C)} \quad (3)$$

in which:
- B represents —$CH_2CH_2OX'$, C represents —$(CH_2)_z$—Y', with z=1 or 2,
- X' denotes the —$CH_2CH_2$—COOH group or a hydrogen atom,
- Y' denotes —COOH or the —$CH_2$—CHOH—$SO_3H$ radical,
- $R_{2'}$ denotes an alkyl radical of an acid $R_9$—COOH present in coconut oil or in hydrolysed linseed oil, an alkyl radical, in particular a $C_7$, $C_9$, $C_{11}$, or $C_{13}$ alkyl radical, a $C_{17}$ alkyl radical and its iso form, or an unsaturated $C_{17}$ radical.

These compounds are classified in the *CTFA dictionary*, *5th edition*, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold under the trade name Miranol C2M concentrate by the company Rhône-Poulenc.

In the compositions in accordance with the invention, anionic surfactants are preferably used, and in particular mixtures of anionic surfactants with amphoteric or nonionic surfactants. A particularly preferred mixture is a mixture consisting of at least one anionic surfactant with at least one amphoteric surfactant.

The anionic surfactant used is preferably chosen from ($C_{12}$–$C_{14}$)alkyl sulphates of sodium, of triethanolamine or of ammonium, the ($C_{12}$–$C_{14}$)alkyl ether sulphates of sodium oxyethylenated with 2.2 mol of ethylene oxide, sodium cocoyl isethionate and sodium ($C_{14}$–$C_{16}$)-α-olefin sulphonate, and mixtures thereof, with:

either an amphoteric surfactant such as the amine derivatives known as disodium cocoamphodipropionate or sodium cocoamphopropionate, sold in particular by the company Rhône-Poulenc under the trade name "Miranol C2M Conc." as an aqueous solution containing 38% active material, or under the name Miranol C32;

or zwitterionic surfactant, such as alkylbetaines, in particular the cocoylbetaine sold under the name "Dehyton AB 30" as an aqueous solution containing 32% AM by the company Henkel.

The hydrophobic galactomannan gum(s) used in accordance with the invention is (are) preferably present in proportions of between 0.1 and 10% relative to the total weight of the composition, and in particular between 0.2 and 5%.

The silicone(s) can be used in the compositions in accordance with the invention in proportions generally of between 0.05 and 20%, and preferably between 0.1 and 10%, by weight, relative to the total weight of the composition.

The surfactant(s) is (are) generally used in the compositions in accordance with the invention in sufficient proportions to give the composition a detergent nature, these proportions preferably being between 5 and 50% relative to the total weight of the composition, and in particular between 8 and 35%.

The vehicle, or support, for the detergent compositions according to the invention is preferably water or an aqueous-alcoholic solution of a lower $C_1$–$C_6$ alcohol such as ethanol, isopropanol or butanol or a mixture of water and alkylene glycol such as propylene glycol and glycol ethers.

The detergent compositions according to the invention have a final pH generally of between 3 and 10. Preferably, this pH is between 5.5 and 8. Adjustment of the pH to the desired value can be carried out conventionally by adding a base (organic or inorganic) to the composition, for example aqueous ammonia, sodium hydroxide or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

The compositions in accordance with the invention can contain, in addition to the combination defined above, viscosity modifiers such as electrolytes, or thickeners. Mention may be made in particular of sodium chloride, sodium xylenesulphonate, scleroglucans, xanthan gums, fatty acid alkanolamides, alkanolamides of carboxylic acid alkyl ether optionally oxyethylenated with up to 5 mol of ethylene oxide, such as the product sold under the name "Aminol A15" by the company Chem Y, crosslinked polyacrylic acids and crosslinked acrylic acid/$C_{10}$–$C_{30}$ alkyl acrylate copolymers. These viscosity modifiers are used in the compositions according to the invention in proportions which can range up to 10% by weight relative to the total weight of the composition.

The compositions in accordance with the invention can also contain up to 5% of pearlescent agents or opacifiers that are well known in the state of the art, such as, for example, sodium or magnesium palmitate, sodium or magnesium stearate or hydroxystearate, or acyl derivatives with a fatty chain, such as monostearates or distearates of ethylene glycol or of polyethylene glycol and fatty chain ethers such as distearyl ether or 1-hexadecyloxyoctadodecanol.

The compositions in accordance with the invention can also optionally contain other agents whose effect is to improve the cosmetic properties of the hair or the skin. Mention may be made in this respect of cationic surfactants, anionic or nonionic or cationic or amphoteric polymers, proteins, protein hydrolysates, ceramides, pseudoceramides, hydroxy acids, vitamins, panthenol and plant, animal, mineral or synthetic oils, antidandruff agents, antiseborrhoeic agents and water-soluble or liposoluble sunscreens.

Among the cationic surfactants, mention may be made in particular (non-limiting list) of: optionally polyoxyalkylenated salts of primary, secondary or tertiary fatty amines; quaternary ammonium salts such as tetraalkylammonium, alkylamidoalkyl-trialkylammonium, dialkyldihydroalkylammonium, trialkylbenzylammonium, trialkylhydroxyalkylammonium or alkylpyridinium chlorides or bromides; imidazoline derivatives, fatty diesters of dimethyltrihydroxy-ethylammonium; or amine oxides of cationic nature, the alkyl radicals having from 1 to 4 carbon atoms.

The conditioners of cationic polymer type which can be used in accordance with the present invention can be chosen from any of those known per se as improving the cosmetic properties of hair treated with detergent compositions, namely, in particular, those described in patent application EP-A-0,337,354 and in French patent applications FR-A-2, 270,846, 2,383,660, 2,598,611, 2,470,596 and 2,519,863.

Even more generally, for the purposes of the present invention, the expression "cationic polymer" denotes any polymer containing cationic groups and/or groups which can be ionized into cationic groups.

Among all the cationic polymers which can be used in the context of the present invention, it is preferred to use quaternary cellulose ether derivatives such as the products sold under the name "JR 400" by the company Union Carbide Corporation, cyclopolymers, in particular the dimethyldiallylammonium salt homopolymers and the copolymers of dimethyldiallylammonium salt and of acrylamide, in particular the chlorides sold under the names "Merquat 100", "Merquat 550" and "Merquat S" by the company Merck, cationic polysaccharides and more particularly guar gum modified with 2,3-epoxypropyltrimethylammonium chloride sold under the name "Jaguar C13S" by the company Meyhall.

By way of amphoteric polymer, mention may be made of polymers comprising at least diallyldimethyl- or diallydiethylammonium units and acrylic acid units, such as the products sold under the name Merquat 280 or Merquat 295 by the company Merck;

chitosans partially modified with $C_4$–$C_8$ dicarboxylic acids, such as those described in FR 2,137,684. The degree of modification can be between 30 and 90% by weight relative to the total weight of the chitosan. These chitosans can be totally deacetylated.

According to the invention, the cationic polymer(s) can represent from 0.001% to 10% by weight, preferably from 0.005% to 5% by weight and even more preferably from 0.01% to 3% by weight, of the total weight of the final composition.

The compositions according to the invention can also contain foam synergists such as $C_{10}$–$C_{18}$ 1,2-alkanediols or fatty alkanolamides derived from mono- or diethanolamine.

These compositions can also contain various adjuvants commonly used in cosmetics, such as fragrances, preserving agents, sequestering agents and foam stabilizers that are well known in cosmetics.

Needless to say, persons skilled in the art will take care to select this or these optional additional compound(s), and/or the amounts thereof, such that the advantageous properties intrinsically associated with the combination (washing base+silicone+guar gum) in accordance with the invention are not, or are not substantially, adversely affected by the addition(s) envisaged.

These compositions can be in the form of liquids thickened to a greater or lesser extent, creams or gels and they are mainly suitable for washing and caring for keratin substances such as the skin or the hair.

The compositions according to the invention are preferably used as shampoos for washing and conditioning the hair, and, in this case, they are applied to wet hair in amounts which are efficient to wash it, this application being followed by rinsing with water.

The compositions in accordance with the invention can also be used as shower gels for washing and conditioning the hair and the skin, in which case they are applied to wet skin and hair and are rinsed after application.

The compositions in accordance with the invention can also be used as products for removing make-up from keratin substances such as the skin, the eyelashes and the eyebrows.

A subject of the invention is also a process for washing and conditioning keratin substances such as the hair, which consists in applying an effective amount of a composition as defined above to the said wet substances, and then in rinsing with water, after the composition has optionally been left to stand on the said substances for a period of time.

Concrete, but in no way limiting, examples which illustrate the invention will now be given.

EXAMPLE 1

A shampoo composition was prepared, containing:

| | |
|---|---|
| Sodium lauryl ether sulphate (70/30 C12/C14) containing 2.2 mol of ethylene oxide (AM = active material) | 16 gAM |
| Imidazoline-based amphoteric surfactant sold under the name Miranol C2M by the company Rhône-Poulenc at 40% AM | 3.2 gAM |
| Hydroxypropyl guar gum modified with stearyl glycidyl ether, sold under the name Jaguar XC 95-3 by the company Rhône-Poulenc | 0.9 g |
| Polydimethylsiloxane sold under the name Mirasil DM 500,000 by the company Rhône-Poulenc | 2 g |
| Citric acid qs | pH 5.5 |
| Fragrance, preserving agents qs | |
| Demineralized water qs | 100 g |

The composition is stable and has a good rheology.

Shampooing is carried out by applying about 12 g of the composition to premoistened hair. The shampoo is worked into a lather and is then rinsed out thoroughly with water.

The lather is airy and is easy to rinse out.

The hair is easy to comb, feels soft and has volume.

EXAMPLE 2

A shampoo composition was prepared, containing:

| | |
|---|---|
| Sodium lauryl ether sulphate (70/30 C12/C14) containing 2.2 mol of ethylene oxide (AM = active material) | 14 gAM |
| Amphoteric surfactant derived from imidazoline, sold under the name Miranol C2M by the company Rhône-Poulenc, containing 40% AM | 2.8 gAM |
| Polydimethylsiloxane of viscosity 60,000 cSt, sold by the company Dow Corning under the name Fluid DC 200 - 60,000 cSt | 1 g |
| Hydroxypropyl guar gum modified with stearyl glycidyl ether, sold under the name Jaguar XC 95-3 by the company Rhône-Poulenc | 0.75 g |
| Hydroxyethylcellulose crosslinked with epichlorohydrin, and quaternized with trimethylamine, sold under the name Celquat SC 240 by the company National starch | 0.2 g |
| Lauryl alcohol oxyethylenated with 2.5 mol of ethylene oxide | 1.1 g |
| Citric acid qs | pH 5.5 |
| Fragrance, preserving agents qs | |
| Demineralized water qs | 100 g |

The composition is stable and has a good rheology.

Shampooing is carried out by applying about 12 g of the composition to premoistened hair. The shampoo is worked into a lather and is then rinsed out thoroughly with water.

The lather is airy and is easy to rinse out.
The hair is easy to comb, feels soft and has volume.

What is claimed is:

1. A composition for washing and conditioning keratin substances comprising, in a cosmetically acceptable aqueous medium, at least one silicone, at least one surfactant with detergent properties, and at least one hydrophobic galactomannan gum, wherein said at least one hydrophobic galactomannan gum comprises hydrophobic substituents chosen from linear or branched alkyl groups containing from 8 to 60 carbon atoms, linear or branched alkenyl groups containing from 8 to 60 carbon atoms, and mixtures thereof, wherein said alkyl and alkenyl groups can be substituted with one or more hydroxyl groups.

2. A composition according to claim 1, wherein said at least one galactomannan gum contains hydrophilic substituents and hydrophobic substituents.

3. A composition according to claim 1, wherein said at least one galactomannan gum has a total molar substitution of greater than 0.7.

4. A composition according to claim 1, wherein said at least one galactomannan gum comprises from 0.7 to 4 hydrophilic substituents and from 0.0001 to 0.02 hydrophobic substituents per anhydroglucoside unit.

5. A composition according to claim 2, wherein the molar ratio of said hydrophilic substituents to said hydrophobic substituents is between 35:1 and 40,000:1.

6. A composition according to claim 2, wherein the hydrophilic substituents are chosen from $C_1$–$C_4$ alkyl groups, a hydroxymethyl group, a hydroxyethyl group, a hydroxypropyl group, a hydroxybutyl group, a carboxymethyl group, an amino group and a carboxylic group.

7. A composition according to claim 2, wherein said hydrophobic substituents are chosen from linear or branched alkyl groups containing from 8 to 60 carbon atoms, linear or branched alkenyl groups containing from 8 to 60 carbon atoms, and mixtures thereof, wherein said alkyl and alkenyl groups can be substituted with one or more hydroxyl groups.

8. A composition according to claim 2, wherein said hydrophobic substituents are chosen from linear or branched alkyl groups containing from 10 to 32 carbon atoms, linear or branched alkenyl groups containing from 10 to 32 carbon atoms, and mixtures thereof, wherein said alkyl and alkenyl groups can be substituted with one or more hydroxyl groups.

9. A composition according to claim 1, wherein said at least one galactomannan gum is chosen from a guar gum.

10. A composition according to claim 1, wherein said at least one silicone is chosen from a volatile silicone.

11. A composition according to claim 1, wherein said at least one silicone is chosen from polyorganosiloxanes that are insoluble in said composition, and are in the form of an oil, a wax, a resin or a gum.

12. A composition according to claim 1, wherein said at least one silicone is a non-volatile polyorganosiloxanes chosen from polyalkylsiloxanes, polyarylsiloxanes, polyalkylarylsiloxanes, silicone gums, silicone resins, polyorganosiloxanes modified with organofunctional groups, and mixtures thereof.

13. A composition according to claim 12, wherein:

(a) said polyalkylsiloxanes are chosen from polydimethylsiloxanes containing trimethylsilyl end groups;
polydimethylsiloxanes containing dimethylsilanol end groups; and
poly($C_1$–$C_{20}$)alkylsiloxanes, (b) said polyalkylarylsiloxanes are chosen from linear polydimethylmethyl phenylsiloxanes, branched polydimethylmethylphenylsiloxanes, mixtures thereof, and polydimethyidiphenylsiloxanes with a viscosity of between $1 \times 10^{-5}$ and $5 \times 10^{-2}$ m²/s at 25° C., (c) said silicone gums are chosen from polydiorganosiloxanes with weight-average molecular masses ranging from 200,000 to 1,000,000, used alone or in the form of a mixture in a solvent, (d) said silicone resins are chosen from resins comprising at least one of the following units: $R_3SiO_{1/2}$, $R_2SiO_{2/2}$, $RSiO_{3/2}$, and $SiO_{4/2}$, in which R represents a hydrocarbon-based group containing from 1 to 16 carbon atoms or a phenyl group, and (e) said organomodified silicones are chosen from silicones containing in their structure one or more organofunctional groups attached via a hydrocarbon-based radical.

14. A composition according to claim 13, wherein said silicone gums, alone or in the form of a mixture, are chosen from polydimethylsiloxane, polydimethylsiloxane/methylvinylsiloxane, polydimethylsiloxane/diphenylsiloxane, polydimethylsiloxane/phenylmethylsiloxane, polydimethylsiloxane/diphenylsiloxane/methylvinylsiloxanes, mixtures formed from a polydimethylsiloxane hydroxylated at the end of the chaim and a cyclic polydimethylsiloxane, mixtures formed from a polydimethylsiloxane gum and a cyclic silicone, and mixtures formed from polydimethylsiloxanes of different viscosities.

15. A composition according to claim 13, wherein said organomodified silicones are polyorganosiloxanes containing at least one of the following groups:

a) polyethylenoxy groups, polypropylenoxy groups, or mixtures thereof;

b) substituted or unsubstituted amine groups;

c) thiol groups;

d) alkoxylated groups;

e) hydroxyalkyl groups corresponding to the following formula:

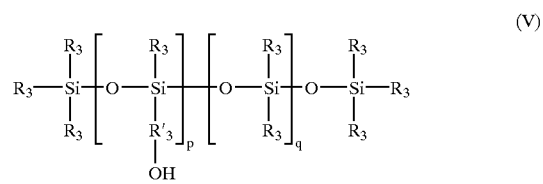

(V)

in which:

said $R_3$ radicals, which may be identical or different, are chosen from methyl radicals and phenyl radicals, with the proviso that at least 60 mol % of the radicals $R_3$ denote methyl radicals;

said $R'_3$ radicals, which may be identical or different, are chosen from a divalent $C_2$–$C_{18}$ hydrocarbon-based alkylene chain unit;

p ranges from 1 to 30; and q ranges from 1 to 150;

f) acyloxyalkyl groups corresponding to the following formula:

$$\text{R}_4\underset{\underset{\text{R}_4}{|}}{\overset{\overset{\text{R}_4}{|}}{\text{Si}}}-\text{O}-\left[\underset{\underset{\text{OCOR}_5}{|}}{\overset{\overset{\text{R}'_4}{|}}{\text{Si}}}-\text{O}\right]_p\left[\underset{\underset{\text{OH}}{|}}{\overset{\overset{\text{R}'_4}{|}}{\text{Si}}}-\text{O}\right]_q\left[\underset{\underset{\text{R}'_4}{|}}{\overset{\overset{\text{R}'_4}{|}}{\text{Si}}}-\text{O}\right]_r\underset{\underset{\text{R}_4}{|}}{\overset{\overset{\text{R}_4}{|}}{\text{Si}}}-\text{R}_4 \quad (\text{VI})$$

in which:
said $R_4$ radicals, which may be identical or different, are chosen from methyl radicals, phenyl radicals, an —$OCOR_5$ radical and a hydroxyl radical;
said $R'_4$ radicals, which may be identical or different, are chosen from methyl radicals and phenyl radicals;
said $R_5$ radicals, which may be identical or different, are chosen from a $C_8$–$C_{20}$ alkyl radical and an alkenyl radical;
said R" radicals, which may be identical or different, are chosen from a linear or branched, divalent $C_2$–$C_{18}$ hydrocarbon-based alkylene radical;
r ranges from 1 to 120;
p ranges from 1 to 30; and
q is equal to 0 or is less than 0.5 p,
with the provisos that:
(i) only one of said $R_4$ radicals per silicon atom may be a hydroxyl group;
(ii) at least 60 mol % of all of said $R_4$ and $R'_4$ radicals denote methyl;
(iii) p+q ranges from 1 to 30; and
(iv) said polyorganosiloxanes of formula (VI) can contain groups:

$$CH_3-\underset{\underset{\underset{|}{O}}{|}}{\overset{\overset{|}{}}{\text{Si}}}-OH$$

in proportions not exceeding 15% of the sum p+q+r;
g) alkycarboxylic groups;
h) 2-hydroxyalkyl sulphonate groups;
i) 2-hydroxyalkyl thiosulphonate groups; and
j) hydroxyacylamino groups.

16. A composition according to claim 1, wherein said at least one silicone is chosen from polyalkylsiloxanes containing trimethylsilyl end groups, polyalkylsiloxanes containing dimethylsilanol end groups, polyalkylarylsiloxanes, polyorganosiloxane resins, polysiloxanes with amino groups, mixtures of at least one polydimethylsiloxane gum and at least one polydimethylsiloxane oil having different viscosities, and mixtures of organosiloxanes and cyclic silicones.

17. A composition according to claim 1, wherein said at least one detergent surfactant is chosen from anionic surfactants, amphoteric surfactants and nonionic surfactants.

18. A composition according to claim 17, wherein said at least one detergent surfactant is a mixture of anionic surfactants with amphoteric surfactants or a mixture of anionic surfactants with nonionic surfactants.

19. A composition according to claim 1, wherein said at least one silicone is present in said composition in an amount ranging from 0.05% to 20% by weight, relative to the total weight of said composition.

20. A composition according to claim 1, wherein said at least one silicone is present in said composition in an amount ranging from 0.1% to 10% by weight, relative to the total weight of said composition.

21. A composition according to claim 1, wherein said at least one hydrophobic galactomannan gum is present in said composition in an amount ranging from 0.1% to 10% by weight, relative to the total weight of said composition.

22. A composition according to claim 1, wherein said at least one hydrophobic galactomannan gum is present in said composition in an amount ranging from 0.2% to 5% by weight, relative to the total weight of said composition.

23. A composition according to claim 1, wherein said at least one surfactant is present in said composition in a amount sufficient to give said composition a detergent nature.

24. A composition according to claim 23, wherein said at least one surfactant is present in said composition in an amount ranging from 5% and 50% by weight, relative to the total weight of said composition.

25. A composition according to claim 23, wherein said at least one surfactant is present in said composition in an amount ranging from 8% and 35% by weight, relative to the total weight of said composition.

26. A composition according to claim 1, wherein said cosmetically acceptable aqueous medium comprises water, or a mixture of water and a cosmetically acceptable solvent chosen from lower alcohols, alkylene glycols and glycol ethers.

27. A composition according to claim 1, wherein said composition further comprises a cationic polymer.

28. A composition according to claim 1, wherein said keratin substances are chosen from hair and skin.

29. A shampoo comprising at least one composition according to claim 1.

30. A shower gel comprising at least one composition according to claim 1.

31. A process for washing and conditioning keratin substances comprising applying to said keratin substances at least one composition according to claim 1, optionally leaving said at least one composition to stand on said keratin substances, and rinsing said treated keratin substances with water.

32. A process for suspending at least one silicone in a washing and conditioning composition comprising, in a cosmetically acceptable aqueous medium, said at least one silicone and at least one surfactant, said process comprising adding at least one hydrophobic galactomannan gum to said washing and conditioning composition,
wherein said at least one hydrophobic galactomannan gum comprises hydrophobic substituents chosen from linear or branched alkyl groups containing from 8 to 60 carbon atoms, linear or branched alkenyl groups containing from 8 to 60 carbon atoms, and mixtures thereof, wherein said alkyl and alkenyl groups can be substituted with one or more hydroxyl groups.

* * * * *

UNITED STATES PATENT AND TRADEMARK OFFICE
CERTIFICATE OF CORRECTION

PATENT NO.   : 6,387,855 B1
DATED        : May 14, 2002
INVENTOR(S)  : Roland de la Mettrie It is certified that error appears in the above-identified patent and that said Letters Patent is hereby corrected as shown below:

Column 13,
Line 54, "polyorganosiloxanes" should read -- polyorganosiloxane --.

Column 14,
Line 2, "polydimethyidiphenylsiloxanes" should read
-- polydimethyldiphenylsiloxanes --.
Line 28, "chaim" should read -- chain --.

Column 15,
Line 42, "alkycarboxylic" should read -- alkylcarboxylic --.

Column 16,
Lines 17 and 18, "a amount" should read -- an amount --.

Signed and Sealed this

Third Day of September, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,387,855 B1  Page 1 of 1
DATED : May 14, 2002
INVENTOR(S) : Roland de la Mettrie It is certified that error appears in the above-identified patent and that said Letters Patent is hereby corrected as shown below:

Column 13,
Line 54, "polyorganosiloxanes" should read -- polyorganosiloxane --.

Column 14,
Line 2, "polydimethyidiphenylsiloxanes" should read
-- polydimethyldiphenylsiloxanes --.
Line 28, "chaim" should read -- chain --.

Column 15,
Line 42, "alkycarboxylic" should read -- alkylcarboxylic --.

Column 16,
Lines 17 and 18, "a amount" should read -- an amount --.

Signed and Sealed this

Fourteenth Day of January, 2003

JAMES E. ROGAN
*Director of the United States Patent and Trademark Office*